United States Patent [19]

Yamashita et al.

[11] Patent Number: 5,023,894
[45] Date of Patent: Jun. 11, 1991

[54] DATA CORRECTING DEVICE FOR USE WITH COMPUTED TOMOGRAPHY APPARATUS

[75] Inventors: Takaji Yamashita; Mitsuo Watanabe; Hiroyuki Okada; Keiji Shimizu, all of Shizuoka, Japan

[73] Assignee: Hamamatsu Photonics K.K., Shizuoka, Japan

[21] Appl. No.: 473,746

[22] Filed: Feb. 2, 1990

[30] Foreign Application Priority Data

Feb. 7, 1989 [JP] Japan .................................. 1-28230

[51] Int. Cl.$^5$ .............................................. A61B 6/00
[52] U.S. Cl. ........................................ 378/4; 378/8; 378/162; 378/901; 358/111
[58] Field of Search ................. 378/4, 20, 8, 162, 163, 378/901; 358/111

[56] References Cited

U.S. PATENT DOCUMENTS

| | | | |
|---|---|---|---|
| 4,403,289 | 9/1983 | Lux et al. | 378/901 |
| 4,580,219 | 4/1986 | Pelc et al. | 378/901 |
| 4,654,795 | 3/1987 | Shimoni | 378/901 |

OTHER PUBLICATIONS

Kubota, K. et al., "The Device of Head Holding Apparatus for CT", pp. 309–315.
"3-Dimensional Coordinates Computing Method of Optical Axis Non-Intersection Type Using Semiconductor Cameras and Its Precision", pp. 17–20.
Adachi, T. et al., "Detecting Method of Position/Direction of a Robot Hand Using PSD and Its Applications", pp. 3–12.
Kasai, T. et al., "Measurement System of 3-D Motion Using a Pair of Position Sensing Detector Cameras", pp. 61–67.
Japanese Patent Application Unexamined Publication No. 42801/1987, corresponding to Japanese Patent Application No. 182811/1985, filed on Aug. 20, 1985.

*Primary Examiner*—Edward P. Westin
*Assistant Examiner*—Kim-Kwok Chu
*Attorney, Agent, or Firm*—Finnegan, Henderson, Farabow, Garrett, and Dunner

[57] ABSTRACT

A data correcting device is intended to be used with a CT apparatus for obtaining a tomographic image with a subject holding means being adapted to be slidable into or out of the tunnel in a gantry. The device includes a body movement sensor for detecting a movement of a subject under examination; a body movement data processing unit for converting body movement data from the body movement sensor into address correcting data; a tomographic data processing unit for processing tomographic data obtained in the gantry; an address converting unit for correcting the address of the tomographic data with the address correcting data; and a memory for storing data.

5 Claims, 4 Drawing Sheets

DATA CORRECTING DEVICE FOR USE WITH COMPUTED TOMOGRAPHY APPARATUS

BACKGROUND OF THE INVENTION

The present invention relates to a data correcting device for use with a computed tomography (CT) apparatus. More particularly, the present invention relates to a device with which the data of measurement in a CT apparatus such as a positron or X-ray CT apparatus is automatically corrected whenever a subject under examination moves his body.

Examination with a positron CT apparatus and other CT apparatus usually takes from several tens of minutes to several hours, during which time a subject must remain in the same posture. If he moves at any instant of the examination, data is disturbed and the image reconstructed from the disturbed data either appears blurred or contains an unnatural noise pattern called an "artifact".

This problem has conventionally been solved by two methods. In one method, the part of the subject to be examined is fixed as long as the examination continues. In the other method, the operator monitors the subject with a TV camera or some other suitable device and returns his body to the correct position as soon as a body movement is detected.

In the first method, the subject's body is fixed to the bed with belts or his head to be examined is fixed with a mask.

A typical method of monitoring the subject is shown in FIG. 7. Before starting a measurement, the subject is imaged with a TV camera and displayed as a still image (indicated by the solid line). If the subject's body moves during the measurement, the resulting image is superposed on the still image (as shown by the dashed line) and either the operator or the subject himself makes the necessary adjustment to bring the current image into registry with the still image.

The first approach in which the subject is fixed as long as the measurement continues involves painful procedures and is not applicable to a subject suffering from a disease. Further, the fixing of the subject is by no means perfect and inevitable movements of the subject's body have deteriorated the reconstructed image. In addition, if a measurement is conducted to obtain cerebrophysiological findings, the fixing of the subject causes him a pain and the data acquired might not reflect the normal functions of the brain.

The second approach in which the subject is monitored is principally intended for avoiding a movement of the subject's body and he must be fixed in order to provide a perfect solution by this approach. Further, data obtained when the body moves is not useful at all. In particular, this causes a serious problem in observing the time-dependent change in the distribution of an isotope in the body.

SUMMARY OF THE INVENTION

An object, therefore, of the present invention is to provide a device which is capable of automatic data correction in accordance with movements of the subject's body.

The data correcting device of the present invention is intended to be used with a computed tomography (CT) apparatus for obtaining a tomographic image with a subject holding means being adapted to be slidable into or out of the tunnel in a gantry. This device attains the above-stated object of the present invention by including: a body movement sensor for detecting a body movement of a subject under examination; a body movement data processing unit for effecting conversion of body movement data from the body movement sensor into address correcting data; a tomographic data processing unit for processing tomographic data obtained in the gantry; an address converting unit for correcting the address of the tomographic data with the address correcting data; and a memory for storing data.

The subject on the subject holding means such as a bed is given a certain degree of freedom. With the subject held in this state, data is gathered by means of detectors in the gantry of a CT apparatus. At the same time, a sensor such as a TV camera constantly monitors a marker on the subject to detect any movement of the subject's body. If a movement of the body is detected, data including such information as the magnitude of the movement, its direction and angle is fed to the body movement data processing unit, where it is converted to the address correcting data. The address correcting data is used to correct the address of the tomographic data from the gantry in the address converting unit and the corrected data is stored in the memory. The reconstructed tomographic image is effectively corrected using the body movement data to provide good quality without blur or any other undesirable defects.

In the operation of the device of the present invention, the subject is fixed to the holding means but, in fact, the holding means itself is adapted to be rotatable about an axis close to the body axis so that, during the operation, the subject is given some degree of freedom in movement together with said holding means. Alternatively, the data correction may be performed with the subject being completely free to move.

DETAILED DESCRIPTION OF THE INVENTION

Two embodiments of the present invention are described hereinafter with reference to the accompanying drawings. In a first embodiment, data correction is made with the subject being fixed to the holding means which is adapted to be rotatable about an axis close to the body axis so that the subject is given some degree of freedom in movement together with said holding means. Compared to the case where the subject is completely fixed, the pain to the subject will be considerably relieved if he is given some freedom of movement, although not independently but together with the bed or a headrest.

Figure 1:
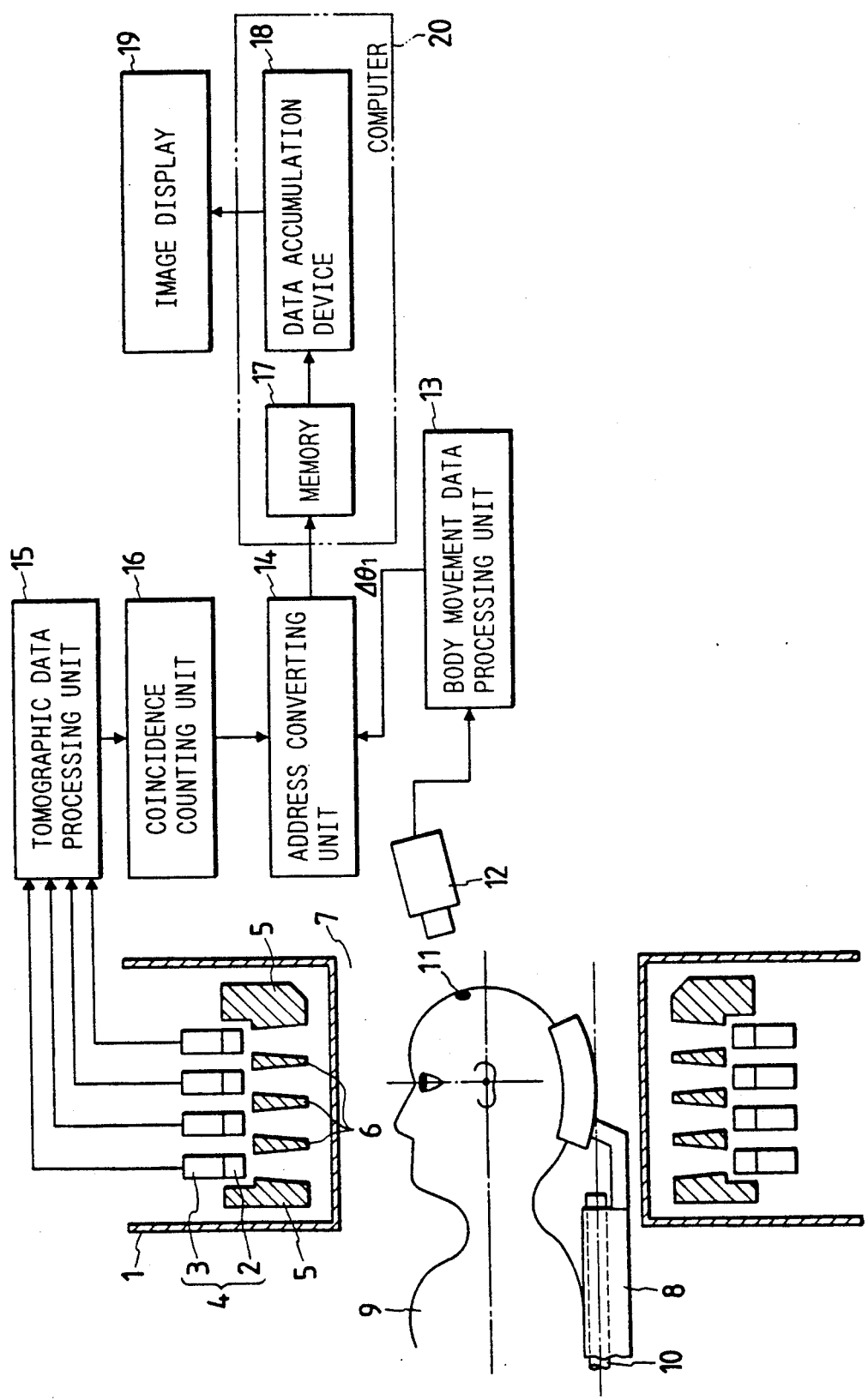
FIG. 1 depicts a data correcting device for use with a CT apparatus according to a first embodiment of the present invention.

In FIG. 1, the gantry 1 of a positron CT apparatus consists of a parallel array of ring-like-arranged radiation detectors 4 each composed of a scintillator 2 for detecting gamma-rays and a photomultiplier tube 3. Provided within the gantry 1 are shield collimators 5 and slice collimators 6 for reducing background noise and setting the range of measurement. Subject holding means 8 consisting of a bed, a headrest, etc. is provided in such a way that it is freely slidable into or out of the tunnel 7 in the gantry 1. A subject 9 lies on the holding means 8 and is fixed thereto. The holding means 8 has a rotating shaft 10 close to the body axis of the subject 9, who is given some degree of freedom in rotation about this shaft together with the holding means 8.

The part of the subject 9 to be examined, for example, his head is provided with a marker 11 which is to be monitored with a body movement sensor 12 such as a position-sensitive detector (PSD) or a TV camera. Alternatively, a rotation encoder installed on the rotating part may be used as the body movement sensor. The body movement sensor 12 is coupled to an address converting unit 14 via a body movement data processing unit 13 which converts detected data to address correcting data. Each of the radiation detectors 4 in the gantry 1 is coupled to the address converting unit 14 via a tomographic data processing unit 15 and a coincidence counting unit 16 which detects coincident events, i.e., determines whether temporal signals from two opposing radiation detectors 4 were generated simultaneously. The address converting unit 14 is coupled to an image display 19 via a memory 17 and a data accumulation device 18 in a computer 20.

Figure 2:
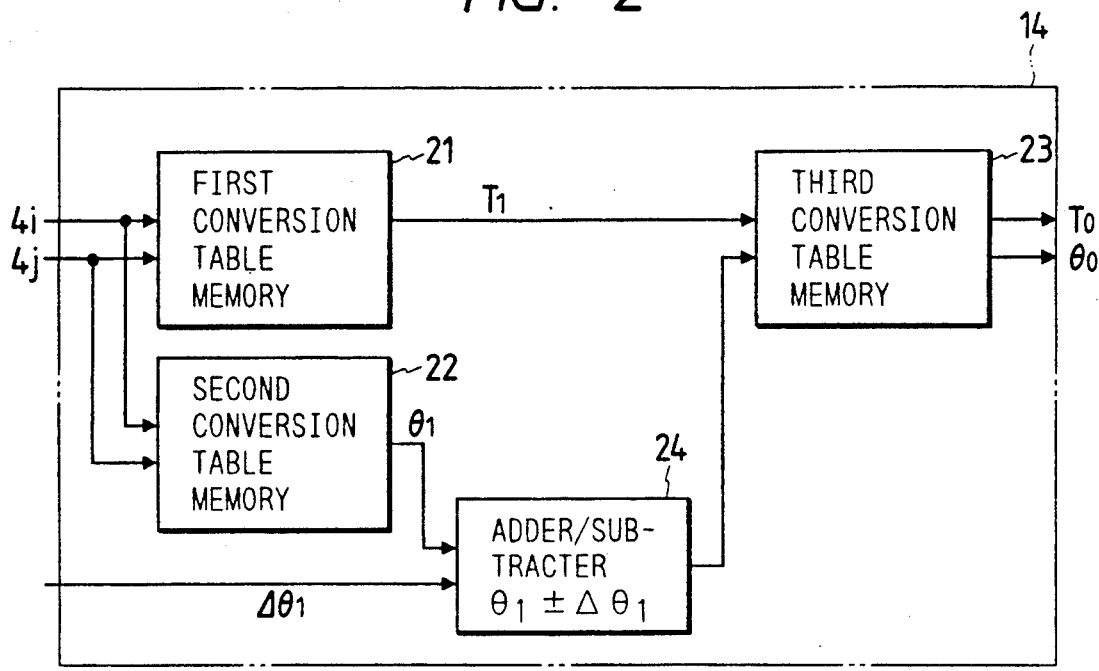
FIG. 2 is a block diagram of the address converting unit in the device.

As shown in FIG. 2, the address converting unit 14 is composed of a first, a second and a third conversion table memory 21, 22 and 23, and an adder/subtracter 24.

The system having the configuration described above will operate in the following manner. The radiation detectors 4 in the gantry 1 detect gamma-ray emissions from the subject 9 and produce output pulse signals. The tomographic data processing unit 15 identifies the time at which each pulse signal was generated and sends temporal signals to the coincidence counting unit 16. At the same time, the unit 15 performs energy discrimination to determine whether the pulse signals are signals caused by gamma-ray photons. The coincidence counting unit 16 determines whether the temporal signals from two opposing radiation detectors $4i$ and $4j$ were generated simultaneously. If yes, these temporal signals are sent to the address converting unit 14.

The body movement sensor 12 such as a TV camera which monitors the marker 11 on the head of the subject 9 sends a signal of rotational angle, $\Delta\theta$, as data on body movement. This rotational angle signal, $\Delta\theta$, is converted to a digital electric signal in the body movement data processing unit 13 and is thence supplied to the address converting unit 14.

Figure 3:
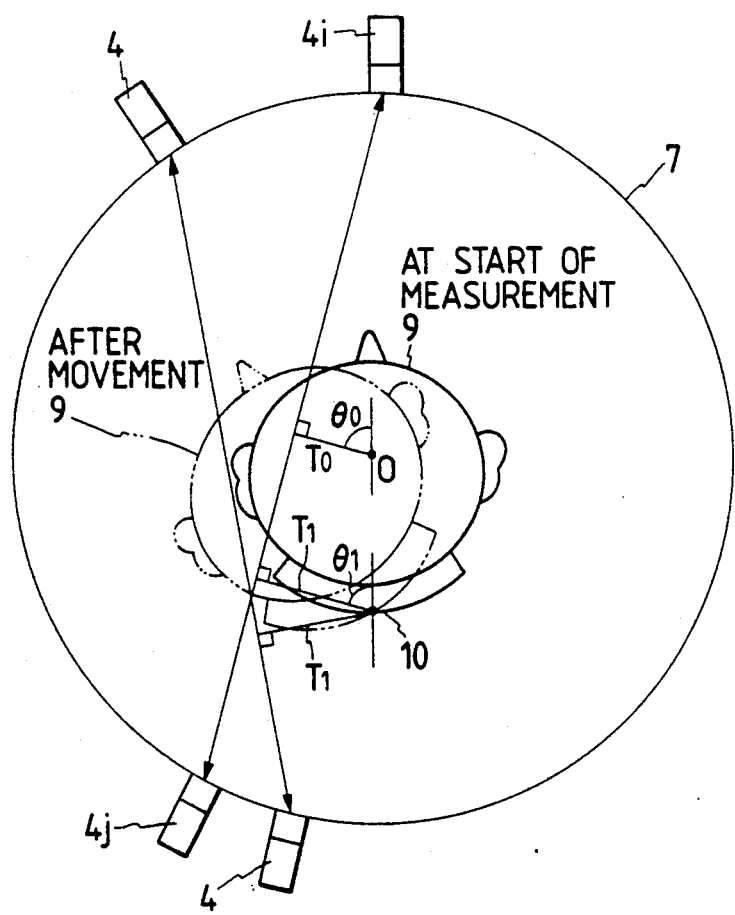
FIG. 3 illustrates the principle of coordinates conversion.

The address converting unit 14 performs address correction in response to movements of the subject's body. As shown in FIG. 3, a positron CT apparatus detects the two gamma-rays which were simultaneously emitted from the subject 9 in opposite directions and data is obtained as a straight line connecting the centers of the two radiation detectors $4i$ and $4j$ that have sensed the coincident emissions. For image reconstructing purposes, said data (radiation detector address pair data) is usually converted to polar coordinate data in the address converting unit 14. Stated more specifically, the addresses of the pair of radiation detectors $4i$ and $4j$ which have detected the coincident emissions are first converted to polar coordinates $(T_1, \theta_1)$ in the first and second conversion table memories 21 and 22, respectively, with the center of coordinates being the rotating shaft 10.

Subsequently, the angular coordinate $\theta_1$ from the second conversion table memory 22 is fed to the adder/subtracter 24 where the angle of deviation, $\Delta\theta$, of the subject 9 as sent from the body movement data processing unit 13 is added to or subtracted from $\theta_1$ to obtain an angular coordinate $(\theta_1 \pm \Delta\theta_1)$ compensating for the body movement. On the other hand, $T_1$ is always equidistant from the rotating shaft 10 and hence remains unchanged despite the body movement.

In the next step, the third conversion table memory 23 performs conversion to polar coordinates $(T_0, \theta_0)$, with the center of coordinates being the central point O of the gantry 1. The data having its address corrected in the way described above is supplied to the data accumulation device 18 via the memory 17 and stored therein. After obtaining all the necessary data, a tomographic image of the examination part is displayed on the image display 19.

A second embodiment of the present invention is such that the subject 9 is free to move without being fixed to the holding means 8 at all. This embodiment is described hereinafter with reference to FIGS. 4–6.

Figure 5:
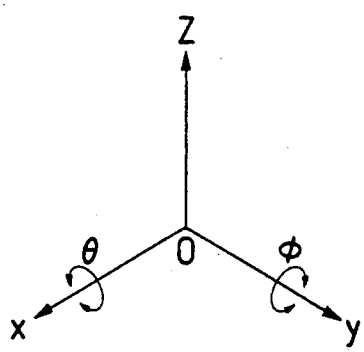
FIG. 5 is an illustration of a coordinate system.

Three or four markers 11 are attached to the head or some other part of the subject 9 to be examined. These markers 11 are monitored with a five-axis movement detecting sensor 12 typically composed of one or more TV cameras. This sensor 12 is intended to obtain three-dimensional (3-D) information on body movements which, as shown in FIG. 5, consists of positional information $\Delta x$, $\Delta y$ and $\Delta z$, as well as rotational information $\Delta\theta$ (angle of rotation about x-axis) and $\Delta\phi$ (angle of rotation about y-axis). The body movement data thus obtained is supplied to the body movement data processing unit 13, where it is converted to digital values hereinafter referred to as "address correcting data".

The address correcting data from the processing unit 13 is used to perform the address correction on the tomographic data in the address converting unit 14, in the manner described above in the first embodiment. The following two methods may be employed to effect the address correction.

First method (histogram mode): Address correcting data resulting from body movements are successively fed to the address converting unit 14 so as to perform consecutive correction of the address of a 3-D data memory into which the tomographic data is to be written.

Second method (list mode): Tomographic data yet to be corrected for a body movement and the corresponding address correcting data are recorded simultaneously and after the acquisition of all data is completed, mathematical operations are performed with a computer to correct each tomographic data.

Figure 6:
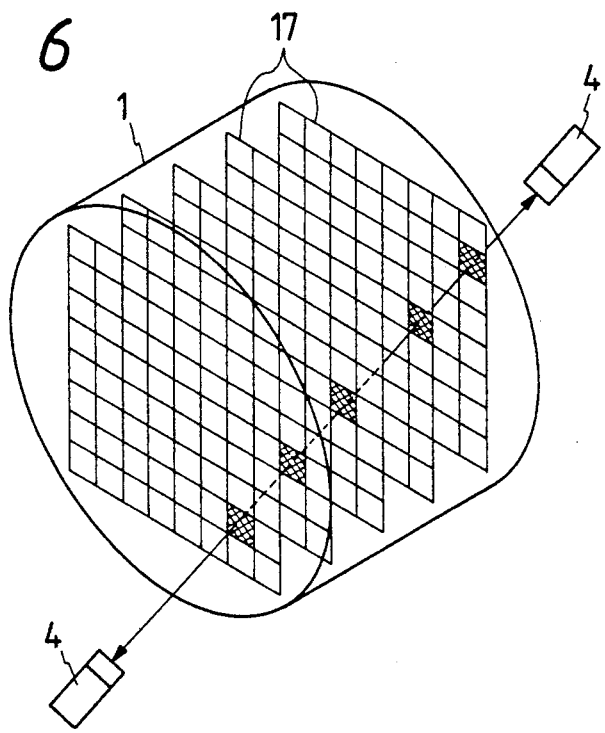
FIG. 6 shows diagrammatically a three-dimensional (3-D) image memory.
Figure 7:
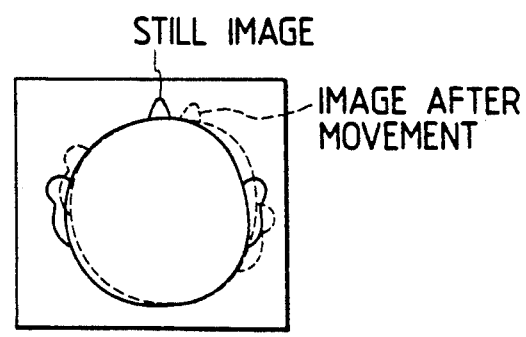
FIG. 7 illustrates the operation of a conventional monitor of body movement.

In the first method, a 3-D image memory for gathering 3-D image data is used as the memory 17. The 3-D image memory may imaginarily be constructed in the gantry 1 as shown in FIG. 6. Data is written into pixels in the respective memory planes in the 3-D image memory that lie on the line connecting two opposing radiation detectors 4 which detected coincident gamma-ray emissions. By repeating this procedure, data is accumulated on the 3-D image memory and a tomographic image is reconstructed upon completion of measurements.

Figure 4:
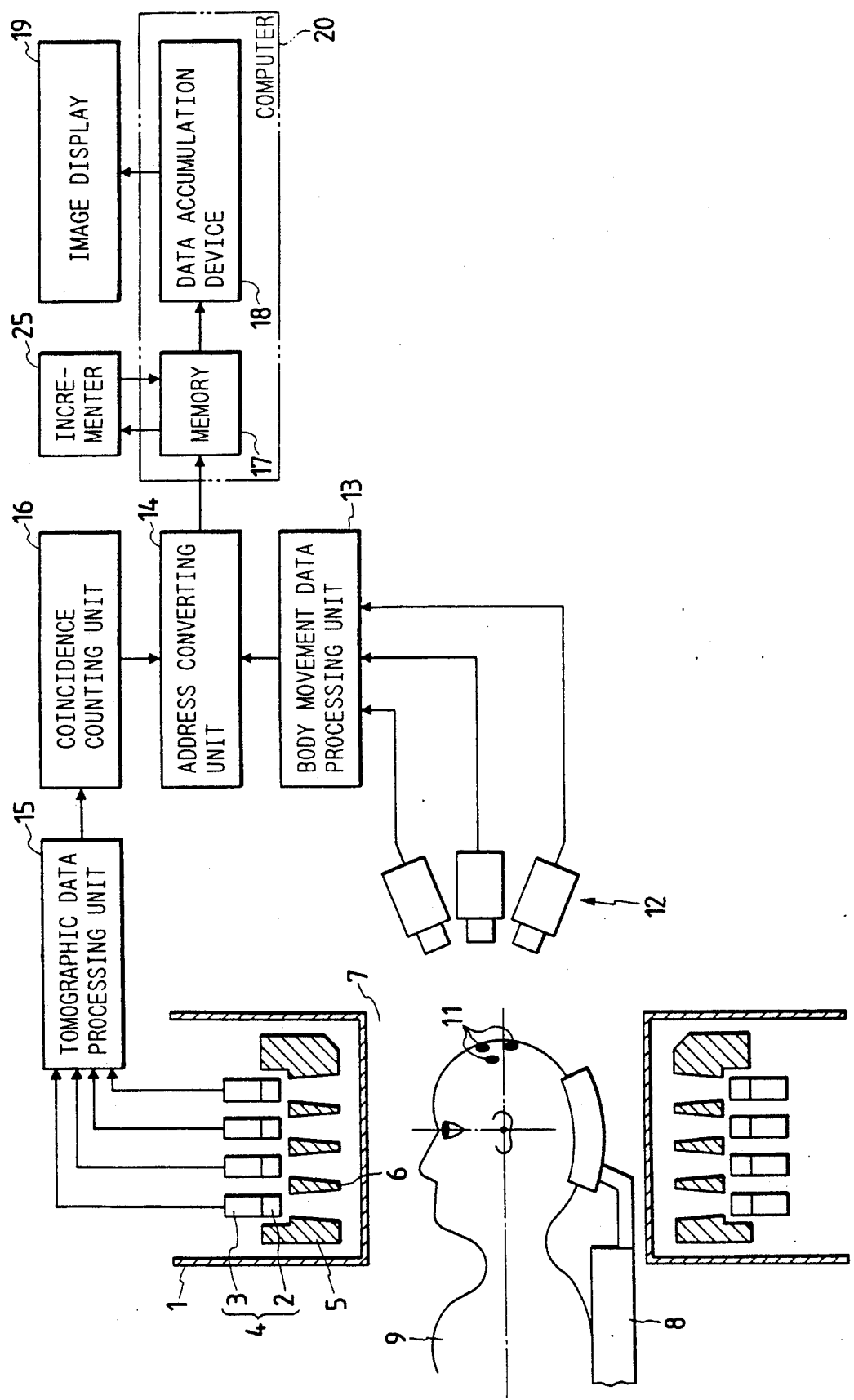
FIG. 4 depicts a data correcting device for use with a CT apparatus according to a second embodiment of the present invention.

If there is no need for address correction, writing of data into the 3-D image memory is executed by the following procedure: as shown in FIG. 4, on the basis of the radiation detector address pair data in the tomographic data processing unit 15, a 3-D memory address generator as the address converting unit 14 designates the addresses of the pixels in the 3-D image memory into which data is to be written, and the memory contents of the designated addresses are read into an incrementer 25 to add new data. If, on the other hand, address correction is to be performed, the addresses of the 3-D image memory into which data is to be written are corrected by means of the address correcting data as supplied from the body movement data processing unit 13.

In the second method, data on the addresses of the pair of detectors that detected coincident emissions of two gamma-rays, i.e., radiation detector address pair data and the corresponding address correcting data are successively recorded on a hard disk for each coincident event, and the recorded data are rearranged and subjected to computation for the data correction after completion of the measurement.

Having the construction described above, the data correcting device of the present invention offers various advantages, five of which are mentioned below:

(1) Reliable data can be obtained consistently as long as examination lasts without causing pains to the subject;

(2) A tomographic image of good quality can be obtained without disturbances from movements of the subject's body;

(3) Even patients and animals that cannot be fixed to a bed for a long period can be examined;

(4) In the absence of pains, the natural physiological state of the brain can be examined correctly; and (5) A positive body movement such as one occurring in physical exercises can be caused to the subject for the purpose of examining the resulting state.

What is claimed is:

1. A data correcting device for use with a computed tomography apparatus for obtaining a tomographic image with a subject holding means being positioned in a gantry, comprising:
    body movement sensing means for detecting a body movement of a subject under examination;
    body movement data processing means for converting body movement data from the body movement sensing means into address correcting data;
    tomographic data processing means for processing tomographic data obtained in the gantry;
    address converting means for correcting an address of the tomographic data with the address correcting data; and
    memory means for storing at least corrected tomographic data.

2. A data correcting device according to claim 1, wherein the subject holding means has a rotating shaft and the body movement sensing means is capable of detecting an angle of rotation of the subject holding means about the rotating shaft caused by the body movement of the subject.

3. A data correcting device according to claim 1, wherein the body movement sensing means is capable of three-dimensional detection of the body movement of the subject, and the memory means comprises a three-dimensional image memory, an address to be accessed of the three-dimensional image memory being corrected with three-dimensional address correcting data produced by the body movement data processing means.

4. A data correcting device according to any one of claims 1, 2 and 3, wherein address correction is effected for each coincident event of radiation emission, and each of the corrected tomographic data is recorded in the memory means.

5. A data correcting device according to any one of claims 1, 2 and 3, wherein the tomographic data and the address correcting data for each coincident event of radiation emission are recorded independently of each other in the memory means, the address of each of the tomographic data is corrected after completion of all measurements.

* * * * *